United States Patent [19]
Reddy

[11] Patent Number: 5,792,097
[45] Date of Patent: Aug. 11, 1998

[54] IONTOPHORETIC ELECTRODES AND SURFACE ACTIVE AGENTS

[75] Inventor: Vilambi Nrk Reddy, Bloomingdale, N.J.

[73] Assignee: Becton Dickinson and Company, Franklin Lakes, N.J.

[21] Appl. No.: 721,877

[22] Filed: Sep. 27, 1996

[51] Int. Cl.⁶ .......................................... A61N 1/30
[52] U.S. Cl. .......................................... 604/20; 607/153
[58] Field of Search ............... 604/19–20; 128/639, 128/640; 607/115, 152, 153; 347/100

[56] References Cited

U.S. PATENT DOCUMENTS

| | | |
|---|---|---|
| 4,088,801 | 5/1978 | Bolon et al. . |
| 4,425,469 | 1/1984 | Emmons et al. . |
| 4,522,211 | 6/1985 | Bare et al. .................. 128/640 |
| 4,536,468 | 8/1985 | Yasui et al. ................. 427/511 |
| 5,320,597 | 6/1994 | Sage, Jr. et al. ............. 604/20 |
| 5,538,789 | 7/1996 | Capote et al. . |
| 5,558,632 | 9/1996 | Lloyd et al. ................. 604/20 |

*Primary Examiner*—Michael Powell Buiz
*Assistant Examiner*—Ellen S. Tao
*Attorney, Agent, or Firm*—Royal N. Ronning, Jr.; Susan A. Capello

[57] ABSTRACT

The present invention relates to improving the utilization of the active mass of printed ink electrodes by adding a surface active agent to at least one of the following the printed ink formulation, the gel formulation, the electrolyte reservoir or the medicament formulation.

4 Claims, 3 Drawing Sheets

IONTOPHORETIC ELECTRODES AND SURFACE ACTIVE AGENTS

BACKGROUND OF INVENTION

The present invention relates to the use of surface active agents to improve the utilization of the active mass in the printed ink electrodes for iontophoretic applications.

Printed ink electrodes for iontophoresis are discussed in U.S. Ser. No. 08/012,168 filed Feb. 2, 1993 (Attorney Docket No. P2374) which is incorporated herein in its entirety. Printed ink electrodes provide a flexible active electrode for an iontophoretic device for delivery of a medicament to a patient, wherein in the electrode is formed from an electrically conductive ink. The printed ink electrode is capable of supporting the iontophoretic electrochemical reactions discussed herein.

Applicant has found that a couple of the problems printed ink electrodes suffer from is under utilization of the electrically active mass contained therein and from non-uniform distribution of current. These problems are due to poor wettability of the active mass with the electrolyte fluid. By way of example and not limitation, Applicant uses for the anode, a Ag printed ink electrode and AgCl cathode electrode. In order for the electrode reaction to take place electrolyte fluid (chloride ion, Cl$^-$) must wet the surface of the active mass of the electrode (Ag), both inside and outside the electrode structure. To achieve sufficient wetting of a surface, the surface tension of that surface must be low. Therefore to achieve sufficient wetting of the surface of the Ag, the surface tension of the Ag must be lowered.

The presence of the surface active agent as claimed by the present invention lowers the surface tension of the Ag and allows the surface of the Ag (both internal and external portions of the Ag of the printed ink electrode) to be wetted by creating a pathway for the electrolyte fluid, Cl$^-$ to reach the active mass of the electrode, Ag. Improving the contact between the electrolyte fluid, Cl$^-$ and the Ag results in more uniform contact between the two and this uniformity results in more efficient and complete utilization of the active mass, Ag in the printed ink electrode.

Some common causes for poor wettability in printed ink electrode formulations is due to the formulation itself, the choice of binders, particle size, shape and or processing (i.e. thermal heat air flow curing of the ink) which results in limiting the electrolyte fluid contact and ion transport. Poor wettability results in the occurrence of "hot spots" or very localized areas of high electrochemical activity. The present invention overcomes some of these limitations through the addition of surface active agents.

SUMMARY OF THE INVENTION

The present invention relates to a printed ink electrode and method of making same as well as a printed ink electrode assembly and method of making same. More specifically the present invention relates to the addition or presence of a surface active agent in the printed ink electrode, printed ink formulation, the drug reservoir, drug formulation, the electrolyte reservoir, the electrolyte formulation or any combination thereof. The surface active agent should be added or present in an amount sufficient for wetting the active mass of the printed ink electrode, such an amount is equal to from about 1.0 to about 0.01 weight percent of the electrode, formulation or reservoir in which it is present or to which it has been added.

DETAILED DESCRIPTION OF THE INVENTION

Applicant has found that the incorporation of surface active agents in the iontophoretic device will improve the printed ink electrode by providing more uniform current delivery and thus, more efficient utilization of the active mass in the printed ink electrode. Prior to Applicant's discovery surface active agents have only been used to enhance skin permeability in the delivery of transdermal drugs.

Utilization of the active mass in the printed ink formulation is defined as the ratio of the experimental to theoretical specific capacities. Specific capacity is defined as the area charge density supported by an electrode for a particular electrode reaction. As the name indicates experimental specific capacity is the result determined by actual experimental procedures. The theoretical specific capacity can be calculated from the specific weight of the active mass (based on area, weight and formulation information), electrode reaction stoichiometry and Faradays Law.

By way of example if a printed ink Ag/AgCl electrode is being used and during iontophoresis the electrodes are brought in contact with chloride ion containing electrolyte, and the current is turned on. The desired electrode reaction at the anode is given by:

$$Ag + Cl^- \rightarrow AgCl + e^- \qquad (1)$$

and the desired reaction at the cathode is given by:

$$AgCl + e^- \rightarrow Ag + Cl^- \qquad (2)$$

For the printed ink electrode to function with the above reactions it is necessary to satisfy the following three conditions:

(i) access to an electronic conductor to supply/remove electrons;

(ii) access to an ionic conductor (electrolyte) to complete the circuit on the solution side; and (iii) access to a supply of reactants (Ag, Cl$^-$, AgCl).

Only in areas of the printed electrode where the above three conditions are simultaneously met, will the active mass be utilized. The active mass in the remaining areas containing active mass in the printed electrode (areas where the three conditions are not met) will be unable to participate in the electrode reaction and thus, the active mass or Ag will not be utilized in those areas.

It is clear based on the foregoing, that improving the accessibility of the electrolyte (Cl$^-$) to the active mass (Ag) will help improve and satisfy conditions (ii) and (iii) thereby improving the utilization of the active mass. Unexpectedly, Applicant has found that the accessibility of the electrolyte to the active mass can be improved by the addition of surface active agents to not only the printed ink formulation, as well as the drug formulation, or the reservoir, which serves to enhance the wettability of the electrode surface and the internal structure of the electrode to the electrolyte.

Figure 1:
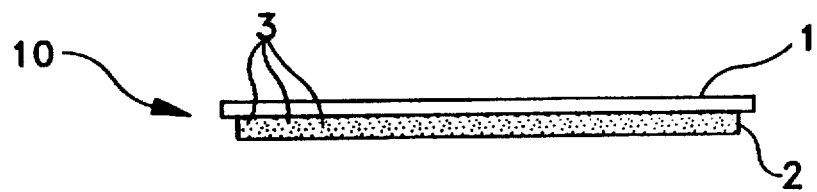
FIG. 1 depicts a schematic representation of a printed ink electrode of the present invention.

One embodiment of the present invention relates to a printed ink electrode for use in an iontophoretic drug delivery device. The printed ink electrode (10) is depicted in FIG. 1 and is made up of a substrate member (1) having applied to it an electrically conductive ink layer (2) having incorporated therein an active mass (3) in sufficient amount to support an iontophoretic electrochemical reaction and a surface active agent in sufficient amount for wetting the active mass (3) of the electrically conductive ink layer (2), said surface active agent being in an amount of from about 1.0 to about 0.01 weight percent of the electrically conductive ink layer (2). This embodiment also anticipates the surface active agent being added in the formulation process of the printed ink electrode (10) in an amount effective for wetting the active mass (3) of the electrically conductive ink layer (2).

Figure 2:
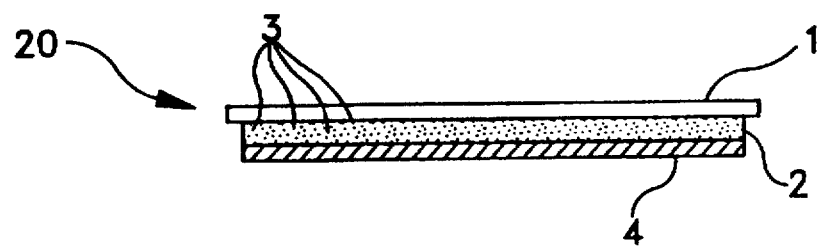
FIG. 2 depicts a schematic representation of a printed ink electrode assembly of the present invention.

Another embodiment of the present invention relates to a printed ink electrode assembly for use in an iontophoretic drug delivery device. The printed ink electrode assembly (20) is depicted in FIG. 2 and is made up of a substrate member (1) having applied to it an electrically conductive ink layer (2) having incorporated therein an active mass (3) in sufficient amount to support an iontophoretic electrochemical reaction and said electrically conductive ink layer (2) being in electrical communication with a drug reservoir (4), wherein said drug reservoir (4) contains a surface active agent in an amount from about 1.0 to about 0.01 weight percent of the drug reservoir (4), such amount being effective for wetting the active mass (3) of the electrically conductive ink layer (2). This embodiment also anticipates the surface active agent being added to the medicament formulation in amount effective for wetting the active mass (3) of the electrically conductive ink layer (2). The present invention also anticipates the surface active agent being added to the gel formulation of the medicament or drug reservoir, where the surface active agent is added in an amount effective for wetting the active mass of the electrically conductive ink layer.

Figure 3:
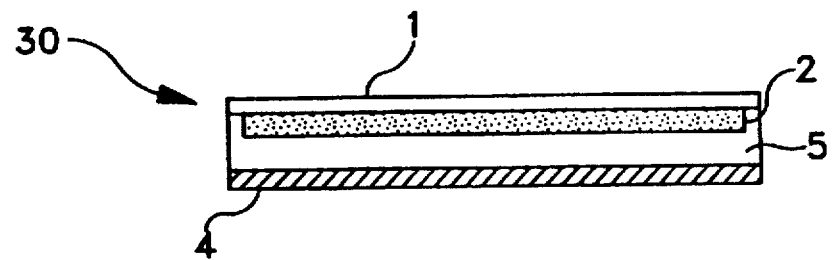
FIG. 3 depicts a schematic representation of a printed ink electrode assembly of the present invention.

Another embodiment of the present invention relates to a printed ink electrode assembly for use in an iontophoretic drug delivery device. The printed ink electrode assembly (30) is depicted in FIG. 3 and is made up of a substrate member (1) having applied to it an electrically conductive ink layer (2) having incorporated therein an active mass (3) in sufficient amount to support an iontophoretic electrochemical reaction and an electrolyte reservoir (5) in electrical communication with said electrically conductive ink layer (2), wherein said electrolyte reservoir (5) contains a surface active agent in an amount from about 1.0 to about 0.01 weight percent of the electrolyte reservoir (5), the amount being effective for wetting the active mass of the electrically conductive ink layer (2). This embodiment also anticipates the surface active agent being added to the electrolyte formulation itself, where the surface active agent is added in an amount effective for wetting the active mass (3) of the electrically conductive ink layer (2). The present invention also anticipates the surface active agent being added to the gel formulation of the electrolyte formulation or reservoir, where the surface active agent is added in an amount effective for wetting the active mass of the electrically conductive ink layer.

Another embodiment of the present invention provide a method for forming a printed ink electrode for use in an iontophoretic drug delivery device. The method involves preparing an electrically conductive ink having incorporated therein, an active mass in sufficient amount to support an iontophoretic electrochemical reaction. Adding to the electrically conductive ink a surface active agent in sufficient amount for wetting the active mass of the electrically conductive ink, the surface active agent being in an amount of from about 1.0 to about 0.01 weight percent of the electrically conductive ink. A substrate member is provided applied to the substrate member is the electrically conductive ink.

Another embodiment of the present invention is a method for forming a printed ink electrode assembly for use in an iontophoretic drug delivery device. The method involves preparing an electrically conductive ink having incorporated therein, an active mass in sufficient amount to support an iontophoretic electrochemical reaction. A substrate member is provided and electrically conductive ink is applied to the substrate member. Also applied to said substrate member a drug reservoir which is in electrical communication with the electrically conductive ink. A surface active agent is added to the drug reservoir in an amount sufficient for wetting the active mass of the electrically conductive ink, said surface active agent being in an amount of from about 1.0 to about 0.01 weight percent of the electrically conductive ink.

Another embodiment of the present invention provides a method for forming a printed ink electrode assembly for use in an iontophoretic drug delivery device. The method again involves preparing an electrically conductive ink having incorporated therein, an active mass in sufficient amount to support an iontophoretic electrochemical reaction, providing a substrate member and applying to the substrate member the electrically conductive ink and also applying to the substrate member an electrolyte reservoir which is in electrical communication with said electrically conductive ink. Added to the electrolyte reservoir is a surface active agent in sufficient amount for wetting the active mass of the electrically conductive ink, the surface active agent being in an amount of from about 1.0 to about 0.01 weight percent of the electrically conductive ink.

Desirable characteristics of the surface active agents for use in the present invention in iontophoretic devices include: (i) non-ionic agents (ii) high molecular weight, considerably higher than the drug being delivered (iii) medical history (iv) non-irritating to skin (v) non-sensitizing to the skin (vi) inexpensive (vii) easy to formulate with electrode ink but not electrochemically active, i.e. it will not undergo oxidation or reduction when the device is in use. Examples of classes of surface active agents to be considered include, but are not limited to: Polysorbates (such as Tween™ type products), Alkyl Ethers (such as Brij™, Texofor™ and Arosur™ type products), Aryl Ethers( such as Triton™ and Rewopal™ type products), Poloxamers (such as Pluronic™ type products) and mixtures thereof.

It is believed that any of these embodiments alone or any combination of the embodiments of the present invention would be sufficient to achieve the results intended herein. It is also believed that the addition of the surface active agent as described does not pose any risk to the patient and that the surface active agent would not interfere with the delivery of the medicament. Applicants reasoning is based on the fact that surface active agents of the present invention are: (i) medically safe, (ii) nonionic, so they won't carry current, (iii) large molecules compared to the medicaments usually being delivered, so they won't be delivered by dissolution, (iv) non-irritant to skin and (v) not electrochemically active.

EXAMPLES

Specific capacity measurements were done with printed ink electrode samples as per standard procedure described as follows:

The electrolyte was 150 mM saline and BDTS wire reference electrodes were used for monitoring the single electrode potentials. Electrode test samples (4 cm×1 cm) were cut from the same sheet of printed Ag/AgCl ink material and the exposed area was 2 cm$^2$. The test current density was set at 4 mA/cm$^2$. TRITONX-100 was used as the surface active agent and specific capacity measurement experiments were done with and without the addition of the surface active agent.

Figure 4:
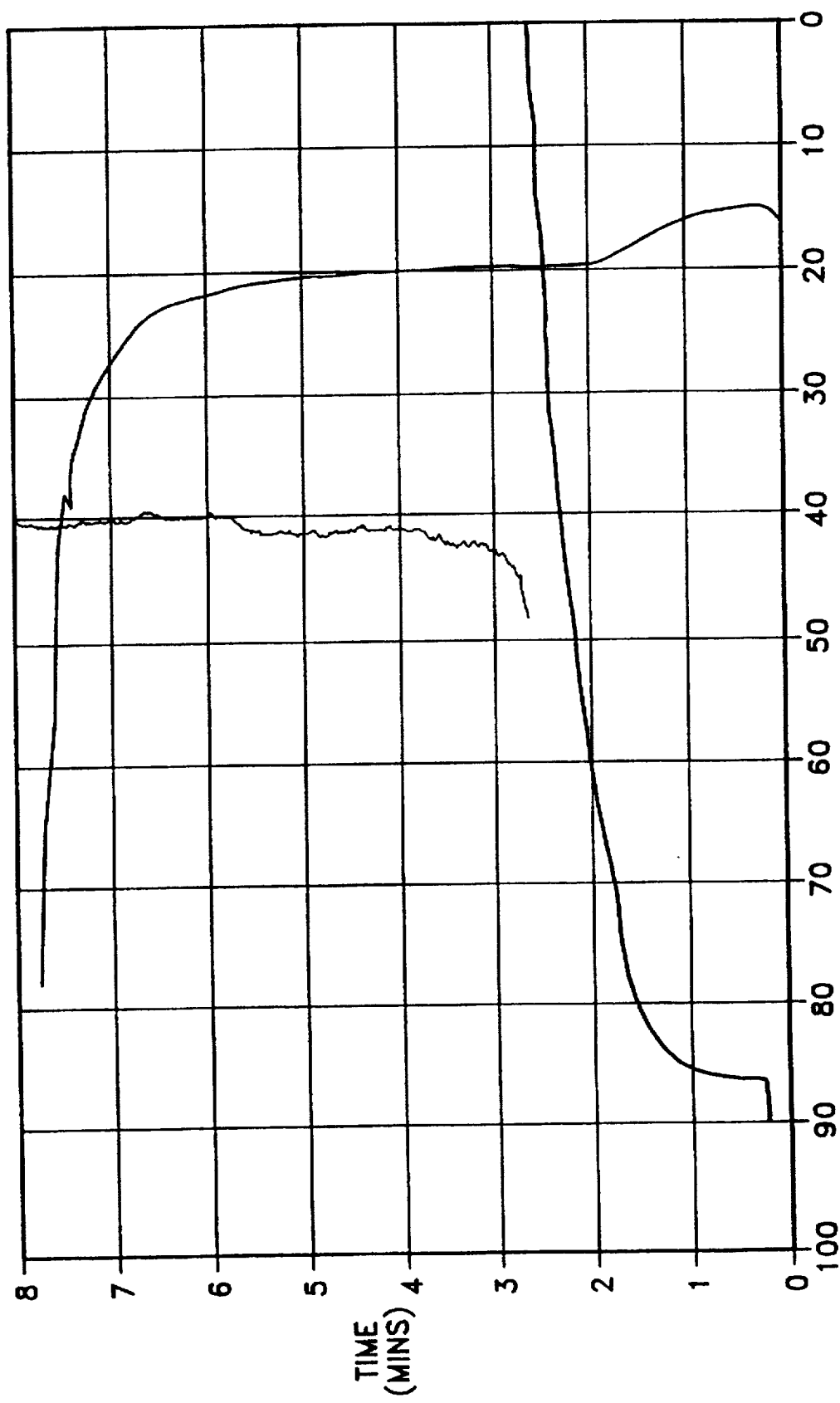
FIG. 4 presents the single electrode potential data with no surface active agent added.

FIG. 4 presents the single electrode potential data with no surface active agent added. At start the anode and cathode polarizations were very low (<100 mV). But within 2 to 3 minutes the anode polarization increased rapidly resulting in very low specific capacities for the anode. Post examination of the anode revealed only surface chloriding and unused Ag underneath suggesting very poor utilization of the active material. Likewise the cathode polarization also increased from 100 to 200 mV at 2 to 3 minutes but leveled off until it eventually died at 7–8 minutes. The increased polarization can be attributed to poor surface properties of the active mass in the electrode structure.

The performance analysis for the electrodes is presented below. Based on the weight loading and formulation information, the theoretical specific capacity of the electrodes was calculated to be 72.5 mA.min/cm$^2$ for the anode and 29.32 mA.min/cm$^2$ for the cathode. The experimental anode specific capacity was determined to be 8.0 mA.min/cm$^2$ resulting in only 11.03% utilization of Ag at the anode.

The poor performance of the electrodes in terms of increased polarization and decreased specific capacities is attributed to poor electrolyte transport into and out of the electrode structure resulting in poor accessibility of electrolyte to the active mass. As suggested by the data, this phenomenon is more severe in the case of the anode where the electrolyte not only provides the ionic transport media but also supplies the chloride ion reactant. Hence addition of surface active agents will improve the wettability of the electrode surface/structure resulting in enhanced electrolyte transport and improved electrode performance.

To illustrate the role played by the surfactant and its effect on the electrode performance, specific capacity measurement experiments were repeated with electrode samples cut from the same sheet of printed ink material as tested in FIG. 4. Testing conditions in terms of electrode size, electrolyte and current density were identical to FIG. 1. However, as the anode polarization started to increase at the end of 2–3 minutes like before (indicating poor utilization of Ag at the anode), two drops of TRITONX-100 surface active agent was added to the electrolyte and stirred and the experiment continued.

Figure 5:
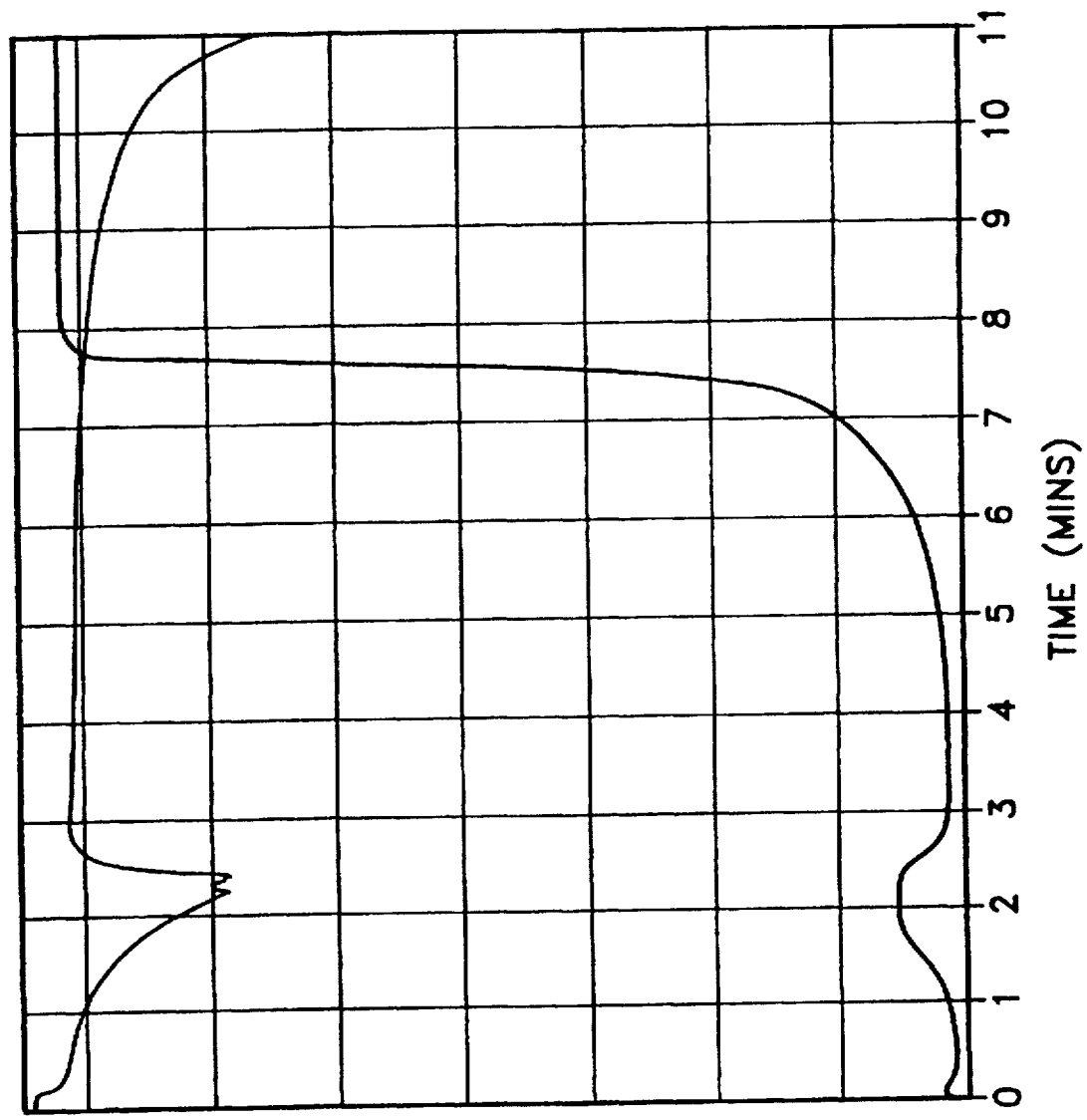
FIG. 5 presents single electrode potential data with the addition of the surface active agent.

FIG. 5 presents single electrode potential data with the addition of the surface active agent. During the initial period (2–3 minutes) prior to the addition of the surface active agent, the performance of the electrode is identical to as in FIG. 1. However, after the addition of the surfactant, the polarization of the anode and cathode reversed and decreased to the level at the start of the experiment and continued for several more minutes indicating improved polarization performance at the electrodes and increased anode specific capacity. Post examination of the anode revealed chloriding through the electrode suggesting improved utilization of the Ag in the electrode.

The performance analysis for the electrodes is presented. Based on the weight loading and formulation information, the theoretical specific capacity of the electrodes was calculated to be 72.5 mA.min/cm$^2$ for the anode and 29.32 mA.min/cm$^2$ for the cathode. The experimental anode specific capacity was determined to be 44.0 mA.min/cm$^2$ resulting in 60.7% utilization of Ag at the anode. Clearly, the presence of surface active agents improved the utilization of Ag at the anode almost six-fold. Also, with the addition of the surface active agent, improvement in polarization performance was observed for both anodes and cathodes.

The improved performance of the electrodes in terms of decreased polarization and increased anode specific capacities is attributed to enhanced electrolyte transport into and out of the electrode structure resulting in good accessibility of electrolyte to the active mass due to the addition of the surfactant. The addition of surface active agent improves the wettability of the electrode surface/structure resulting in enhanced electrolyte transport and improved electrode performance.

This example clearly demonstrates the significant role / effect surface active agents can play in improving the performance and utilization of active mass in printed ink electrodes for iontophoresis. Any improvement m utilization will directly result in decreasing the cost and increasing the robustness of the electrodes. Also, the presence of the surface active agents in the electrode structure will help in uniform electrolyte transport eliminating localized "inactive" areas and improving uniformity of current delivery.

As discussed above the presence of surface active agents significantly improved the performance of the iontophoretic electrodes. Electrode performance testing experiments were done with printed ink Ag/AgCl electrodes with and without the addition of surfactant. It was clearly shown that the utilization of Ag at the anode was increased by almost six-fold in the presence of the surfactant. Also the polarization of the electrode (anode and cathode) was decreased by at least 100 mV by the addition of surfactant. The surface active agents improve the wettability of the electrolyte and enhance accessibility of the electrolyte / reactant to the active material resulting in increased utilizations and decreased polarizations.

I claim:

1. A printed ink electrode assembly for use in an iontophoretic drug delivery device comprising:

an electrically conductive ink layer having incorporated therein an active mass in sufficient amount to support an iontophoretic electrochemical reaction and said electrically conductive ink layer being in electrical communication with a drug reservoir, wherein said drug reservoir contains a surface active agent in an amount from about 1.0 to about 0.01 weight percent of the drug reservoir, such amount being effective for wetting the active mass of the electrically conductive ink layer; wherein the surface active agent is a surfactant is selected from the group consisting of polysorbates, alkyl ethers, aryl ethers, poloxamers and mixtures thereof; and wherein the electrically conductive ink layer contains an amount of a surface active agent effective for wetting the electrically conductive ink layer.

2. A printed ink electrode assembly for an iontophoretic drug delivery device comprising:

an electrically conductive ink layer having incorporated therein an active mass in sufficient amount to support an iontophoretic electrochemical reaction and an electrolyte reservoir in electrical communication with said electrically conductive ink layer, wherein said electrolyte reservoir contains a surface active agent in an amount from about 1.0 to about 0.01 weight percent of the electrolyte reservoir, the amount being effective for wetting the active mass of the electrically conductive ink layer; wherein the surface active agent is a surfactant selected from the group consisting of polysorbates, alkyl ethers, aryl ethers, poloxamers and mixtures thereof; and wherein the electrically conductive ink layer contains an amount of a surface active agent effective for wetting the electrically conductive ink layer.

3. A method for forming a printed ink electrode assembly for use in an iontophoretic drug delivery device, comprising:

preparing an electrically conductive ink having incorporated therein, an active mass in sufficient amount to support an iontophoretic electrochemical reaction, providing a substrate member and applying to said substrate member said electrically conductive ink, also applying to said substrate member a drug reservoir which is in electrical communication with said electrically conductive ink, adding to the drug reservoir a surface active agent in sufficient amount for wetting the active mass of the electrically conductive ink, said surface active agent being in an amount of from about 1.0 to about 0.01 weight percent of the electrically conductive ink; wherein the surface active agent is a surfactant selected from the group consisting of polysorbates, alkyl ethers, aryl ethers, poloxamers and mixtures thereof; and adding to the electrically conductive ink an amount of a surface active agent effective for wetting the electrically conductive ink.

4. A method for forming a printed ink electrode assembly for use in an iontophoretic drug delivery device, comprising:

preparing an electrically conductive ink having incorporated therein, an active mass in sufficient amount to support an iontophoretic electrochemical reaction, providing a substrate member and applying to said substrate member said electrically conductive ink, also applying to said substrate member an electrolyte reservoir which is in electrical communication with said electrically conductive ink, adding to the electrolyte reservoir a surface active agent in sufficient amount for wetting the active mass of the electrically conductive ink, said surface active agent being in an amount of from about 1.0 to about 0.01 weight percent of the electrically conductive ink; wherein the surface active agent is a surfactant selected from the group consisting of polysorbates, alkyl ethers, aryl ethers, poloxamers and mixtures thereof; and adding to the electrically conductive ink an amount of a surface active agent effective for wetting the electrically conductive ink.

* * * * *